(12) United States Patent
Burton

(10) Patent No.: US 8,955,401 B1
(45) Date of Patent: Feb. 17, 2015

(54) VEHICLE-MOUNTED SOIL SAMPLING APPARATUS

(76) Inventor: James D. Burton, Little Rock, AR (US)

(*) Notice: Subject to any disclaimer, the term of this patent is extended or adjusted under 35 U.S.C. 154(b) by 865 days.

(21) Appl. No.: 13/080,726

(22) Filed: Apr. 6, 2011

Related U.S. Application Data

(60) Provisional application No. 61/321,425, filed on Apr. 6, 2010.

(51) Int. Cl.
*G01N 1/08* (2006.01)
*E21B 49/02* (2006.01)
*G01N 1/34* (2006.01)
*G01N 1/38* (2006.01)

(52) U.S. Cl.
USPC .......... 73/864.45; 73/863.33; 73/863.91; 73/864.41; 73/864.51; 175/20

(58) Field of Classification Search
CPC ........ E21B 49/02; G01N 1/08; G01N 1/2806; G01N 1/34; G01N 1/38; G01N 2001/021; G01N 2001/2866
USPC ............... 73/863.31, 863.33, 863.91–863.92, 73/864.41, 864.43, 864.45–864.51, 73/864.62; 175/20
See application file for complete search history.

(56) References Cited

U.S. PATENT DOCUMENTS

| | | |
|---|---|---|
| 1,362,968 A | 12/1920 | Stewart |
| 2,565,224 A | 8/1951 | Gibbens |
| 3,084,553 A | 4/1963 | Cullinan et al. |
| 3,224,512 A | 12/1965 | Alexander |
| 3,331,249 A | 7/1967 | Boxrud |
| 3,464,504 A | 9/1969 | Stange |
| 3,625,296 A | 12/1971 | Mabry et al. |
| 4,316,393 A | 2/1982 | Philipenko |
| RE30,901 E | 4/1982 | Boxrud |
| 4,332,301 A | 6/1982 | Jonell |
| 4,333,541 A | 6/1982 | Doty |
| 4,336,849 A | 6/1982 | Hug |
| 4,356,734 A | 11/1982 | Ivancsics |
| 4,482,021 A | 11/1984 | Repski |
| 4,828,047 A | 5/1989 | Rogerson |
| 4,869,115 A | 9/1989 | Edwards et al. |
| 4,989,678 A | 2/1991 | Thompson |
| 5,076,372 A | 12/1991 | Hellbusch |
| 5,211,248 A | 5/1993 | Nosewicz et al. |
| 5,213,169 A | 5/1993 | Heller |
| 5,394,949 A | 3/1995 | Wright et al. |
| 5,435,399 A | 7/1995 | Peterson et al. |
| 5,741,983 A | 4/1998 | Skotnikov et al. |
| 5,887,491 A | 3/1999 | Monson et al. |
| 5,950,741 A | 9/1999 | Wright et al. |
| 5,991,687 A * | 11/1999 | Hale et al. ............... 701/470 |
| 6,016,713 A | 1/2000 | Hale |
| 6,119,531 A | 9/2000 | Wendte et al. |
| 6,237,429 B1 | 5/2001 | Melnyk |

(Continued)

FOREIGN PATENT DOCUMENTS

DE 3612409 A1 * 10/1987 ............. 73/864.41
JP 09065748 A * 3/1997 ............. A01D 34/70

*Primary Examiner* — Thomas P Noland

(57) ABSTRACT

A soil sampling apparatus comprising a motorized vehicle may be used to remove soil samples at intervals over a field of interest. The apparatus comprises a sampling assembly that rotates and extends downwardly into the soil to collect a sample. The probe assembly is raised to dump the sample into a collection assembly, which transfers the sample to a bagging assembly, where the sample may be bagged for later analysis.

20 Claims, 7 Drawing Sheets

(56) References Cited

U.S. PATENT DOCUMENTS

| | | |
|---|---|---|
| 6,260,633 B1 | 7/2001 | Machek et al. |
| 6,360,829 B1 | 3/2002 | Naber et al. |
| 6,363,803 B1 | 4/2002 | Hubers |
| 6,484,654 B2 * | 11/2002 | Chiu .............................. 111/200 |
| 6,766,865 B1 | 7/2004 | Dagel et al. |
| 6,959,245 B2 | 10/2005 | Rooney et al. |
| 7,255,016 B2 | 8/2007 | Burton |
| 7,552,654 B2 | 6/2009 | Burton |
| 7,827,873 B2 * | 11/2010 | Burton ....................... 73/864.45 |
| 2005/0172733 A1 | 8/2005 | Drummond et al. |
| 2013/0319763 A1 * | 12/2013 | McGraw ......................... 175/20 |

* cited by examiner

VEHICLE-MOUNTED SOIL SAMPLING APPARATUS

CROSS-REFERENCE TO RELATED APPLICATIONS

This application claims the benefit of U.S. provisional patent application Ser. No. 61/321,425, filed on Apr. 6, 2010, and entitled "Vehicle-Mounted Soil Sampling Apparatus." Such application is incorporated herein by reference in its entirety.

STATEMENT REGARDING FEDERALLY SPONSORED RESEARCH OR DEVELOPMENT

Not applicable.

BACKGROUND OF THE INVENTION

The present invention relates to soil sampling devices, and in particular to soil sampling devices that may be mounted on a truck, utility vehicle, or the like.

In order to optimize the production capacity of any agricultural land, the grower must provide in each plot of soil the amount of fertilizers and other nutrients and additives that will render each plot ideal for the crop that is to be sewn and harvested. The grower cannot know how much fertilizer or other additives should be placed at a plot of soil, however, without knowing the current level of nutrients and important minerals that are already present in each plot. The quantity of these various materials present will vary greatly depending upon such factors as the soil type, the history of crops grown, and additives that have been previously applied to the field. It is thus a common practice for growers to periodically remove soil samples from various regions on their agricultural lands, which are then analyzed to determine the level of various important nutrients and minerals that they contain. It would also be highly desirable to know the level of compaction of soil in various regions, in order to properly gauge the steps necessary to arrive at the proper level of soil compaction for a particular crop to be grown in each region, although this testing is not commonly performed today.

Soil sampling has historically been a process performed by hand. Various hand tools have been developed to somewhat ease the burden of this task, but any manual operation to perform soil sampling is necessary tiresome and time-consuming because of the expanse of land that must be covered when soil sampling is performed as part of a large-scale commercial farming enterprise. Typically, a worker drives a truck over the area in question, stopping at each designated point and exiting the vehicle to perform the sampling process. Because of the arduous nature of this task, growers typically take only one sample in a field of interest, or at most a few samples across a field or area of interest and then average the results. The farmer will then apply fertilizers and other nutrients to the soil as if the soil's level of nutrients were uniform across the field, which is in fact not generally the case. The result is a poor approximation of the optimal nutrient level for each plot of soil, since some plots will likely be under fertilized and others will be over fertilized. Under fertilized plots will produce poor yields, and over fertilized plots may both produce poorer than optimum yields and also result in a waste of fertilizers. The wasted fertilizer not only is an added expense for the grower, but also exacerbates environmental issues that may arise from the later run-off of the excessive fertilizer due to rain or wind.

With the wide availability of global positioning system (GPS) satellite receivers today, the use of GPS information in soil sampling is rapidly increasing. GPS receivers have in fact become a staple of modern commercial farming equipment. The use of GPS in conjunction with manual soil sampling, however, only provides modest improvements in accuracy and efficiency. Although the grower now has precise information about where each sample is taken, manual sampling procedures still require a worker to travel to each identified point in the field of interest, remove a sample by hand, and then label and transport that sample for analysis. Thus it would be highly desirable to develop a soil sampling system that would allow for the collection of a periodic sample the soil across a field, while automatically keeping track of where samples were removed using GPS information.

The related art includes several attempts to develop soil sampling mechanisms that periodically sample soil over an area. U.S. Pat. No. 3,224,512 to Alexander teaches a soil sampler that is mounted on a trailer and powered by a hydraulic system. The device is intended to be pulled by a tractor around a field, and the motion of one of the vehicle wheels activates a piston and cam-drive arrangement in communication with the soil sampler's hydraulics. Since the sampling periodicity is driven by the motion of one of the wheels on the trailer, the device automatically samples soil at regular intervals, regardless of the speed of the tractor pulling the trailer. The device uses a sampling tube that is forced into the ground for sample collection. Since the device does not stop in order for samples to be taken, the sampling tube is designed to pivot upon entry into the ground. The sampling tube is returned to its original insertion position (angled toward the front of the trailer) by means of a spring.

U.S. Pat. No. 3,625,296 to Mabry et al. teaches another soil sampling device that is mounted on a trailer, and which is intended to periodically sample soil over which the trailer passes. A digger foot is used to collect the soil sample, the foot being mounted at the end of a lever that includes a cam follower at its opposite end. By means of the cam follower, a cam on one of the tractor's wheels forces the digger foot into the ground as the trailer travels, thereby scooping a soil sample. As the cam rolls forward, the digger foot is released and a spring biases the digger foot upward, where it strikes a bumper block and deposits the soil sample into a collection container. Like the Alexander device, the Mabry et al. device automatically samples soil at regular intervals, since its sampling periodicity is driven by the distance traveled by the cam-equipped tractor wheel.

U.S. Pat. No. 5,741,983 to Skotnikov et al. teaches a third trailer-mounted automatic soil sampling device. In this case, an odometer is used to monitor the distance of travel of the trailer, which drives the sampling period of the device. The device utilizes a shaft-drive and linkage arrangement to control the period of the sampling action based upon the rotation of one of the trailer's wheels. A complex linkage arrangement allows the sampling tube to be raised into a position to eject and deposit a sample during each sampling cycle. The device further includes a bagging mechanism, whereby each of the samples that are drawn from the ground may be automatically bagged and labeled for later laboratory analysis.

The sampling mechanisms described above suffer from important disadvantages that have limited their adoption in large commercial farming operations. Mechanisms that simply scoop a sample of material from the top of the ground are undesirable, since such a sample may not be representative of the lower levels of the soil in the area that is sampled. The most relevant section of the soil is that section that will be in greatest contact with the roots of the crop to be planted, which in the case of almost all commercial crops will be soil that lies at some distance below the surface. Further, in many applications the most desirable sample will be one that spans a section of the soil, from the surface to a pre-determined depth beneath the surface. A scooping mechanism will likely be unable to probe deeply enough to produce a sufficient sample to meet this need.

Although sampling mechanisms that insert a tube into the ground to collect a sample are superior to scoop mechanisms in many applications, the tube-type sampling mechanisms known in the art also suffer from important disadvantages. The process of inserting and removing a tube from a moving vehicle presents a number of difficulties. In one case these difficulties have been addressed by the use of a tube that pivots, thereby allowing the tube to be inserted into the ground at a forward-sloped angle, while it pivots rearwardly until the tube is removed. Depending upon the hardness of the soil, however, this may create a great deal of stress upon the tube. The pivoting action causes the tube to push backward against soil that is rearward of the tube at its distal end, and push forward against soil that is forward of the tube at its proximal end. While this may be a workable solution in very loose, highly compressible soil, this will likely lead to bending, excessive wear, or other damage to the tube in more firmly packed soil, such as many clay-based soils, or soil that may contain rocks or other hard obstacles.

Another solution to the problem of vehicle motion while the tube is inserted in the ground is a complex linkage arrangement that allows the structure immediately supporting the sampling tube to "follow" the tube during the portion of the sampling cycle when the tube is inserted into the ground. While this arrangement may avoid the problems presented by tube rotation, the structure and linkages necessary for this functionality are complex, and would likely be expensive to manufacture and difficult to maintain.

U.S. Pat. No. 7,255,016 to the inventor hereof teaches an automated machine that automatically takes soil samples as it is directed across a field of interest. A track is used with a probe that rotates as the track moves in contact with the ground. The machine automatically inserts the probe in the ground, withdraws the probe, and empties soil from the probe during reach revolution. This device solves many of the problems presented with the prior art devices, in that sampling may be continuously performed over an area of interest, and a great number of samples may thus be collected providing a high degree of resolution for the resulting soil analysis on a particular plot. The device is expensive, however, and while its use will likely prove to be cost-effective for larger farms, it is not clear that it will be cost-effective for small farms, where a more simple sampling scheme with fewer samples collected may suffice.

What is desired then is an automatic soil sampling mechanism that facilitates the sampling of soil across an area of interest, while also being inexpensive to manufacture and simple to operate and maintain. The limitations of the prior art are overcome by the present invention as described below.

SUMMARY OF THE INVENTION

The present invention is directed to a soil sampling apparatus that comprises a truck or other vehicle carrying a sampling assembly that is capable of quickly and efficiently removing a sample from the soil when the vehicle stops. It is not required for the driver to exit the vehicle in order to collect a sample. The sample may be dropped from the sampling tube as it passes around the top portion of the mechanism. In various embodiments, soil compaction within the sampling tube may be avoided by tapering of the interior of the tube itself.

Soil cores dropped from the sampling tube fall into a collection trough, which in certain embodiments may include an auger system to direct soil. A pneumatic delivery system may be used in certain embodiments to move collected samples from the collection tray to sample storage bags, which for ease of access may be located adjacent to the operator of the vehicle. In one embodiment, a rotating carousel with multiple bag holders may be employed in order to collect samples. A computer-based GPS mapping system may be used in conjunction with the present invention in order to coordinate the mapping of a field of interest and collection of samples at appropriate locations, as well as guiding the pull vehicle.

It is therefore an object of the present invention to provide for a soil sampling mechanism that may collect soil samples over an area of interest without requiring a driver to exit the vehicle to which the sampling mechanism is attached.

It is also an object of the present invention to provide for a soil sampling mechanism that is inexpensive to produce and easy to maintain.

It is also an object of the present invention to provide for a soil sampling mechanism that allows for the pneumatic movement of collected samples from a collection tray to a location more convenient to an operator.

It is also an object of the present invention to provide for a soil sampling mechanism that allows the collection of a number of soil samples in a plurality of separate bags for later analysis.

It is also an object of the present invention to provide for a soil sampling mechanism that allows for the use of a computer-based mapping system in order to map an area of interest and collect samples from the appropriate portions of the area of interest.

These and other features, objects and advantages of the present invention will become better understood from a consideration of the following detailed description of the preferred embodiments and appended claims in conjunction with the drawings as described following:

DETAILED DESCRIPTION OF THE PREFERRED EMBODIMENTS

Figure 1:
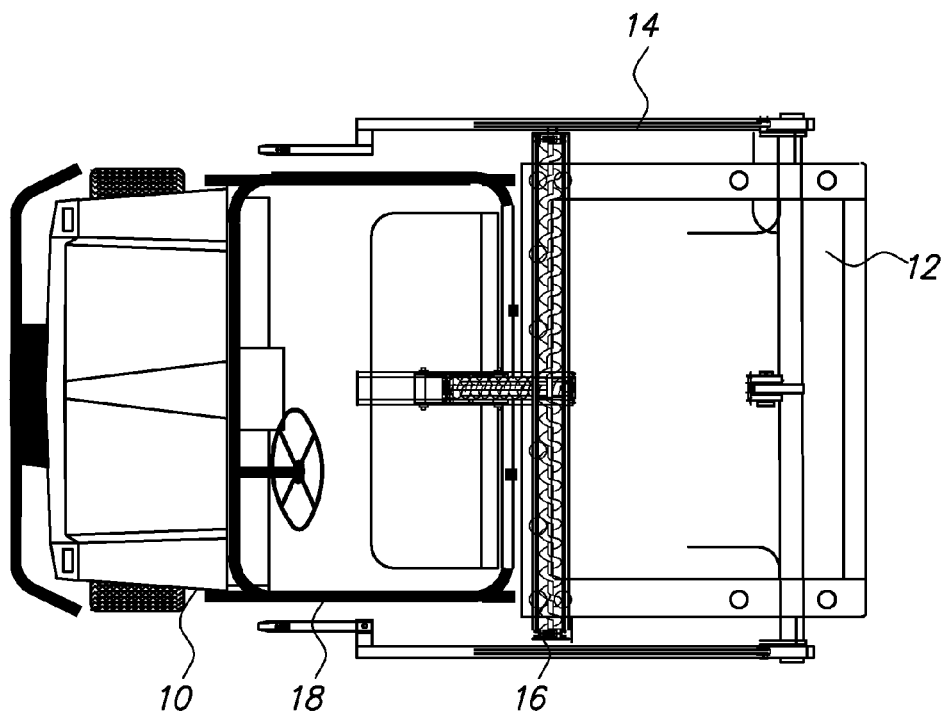
FIG. 1 is a top plan view of a vehicle including a preferred embodiment of the present invention.
Figure 2:
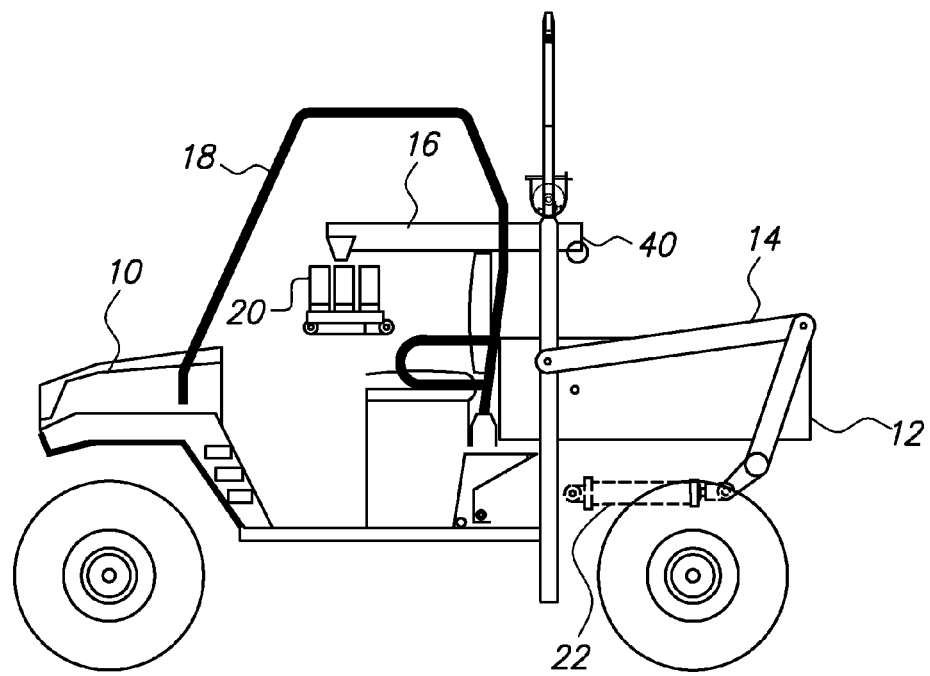
FIG. 2 is a side plan view, in partial cut-away, of a vehicle including a preferred embodiment of the present invention.

With reference to FIGS. 1 and 2, a general description of the preferred embodiment of the present invention may be described. Vehicle 10 may be a truck or any of the sorts of utility vehicles that are commonly used in farming applications. Preferably, vehicle 10 has a bed 12. Sampling assembly 14 and collection assembly 16, the individual components of which will be described in more detail below, are mounted at bed 12, and a portion of collection assembly 16 extends into cab 18 of vehicle 10. Bagging assembly 20 is preferably mounted in cab 18 in order to provide convenient access to collected soil samples for the driver of vehicle 10. Sampling assembly 14 is powered by hydraulic cylinders 22, of which there are two in the preferred embodiment.

Figure 3A:
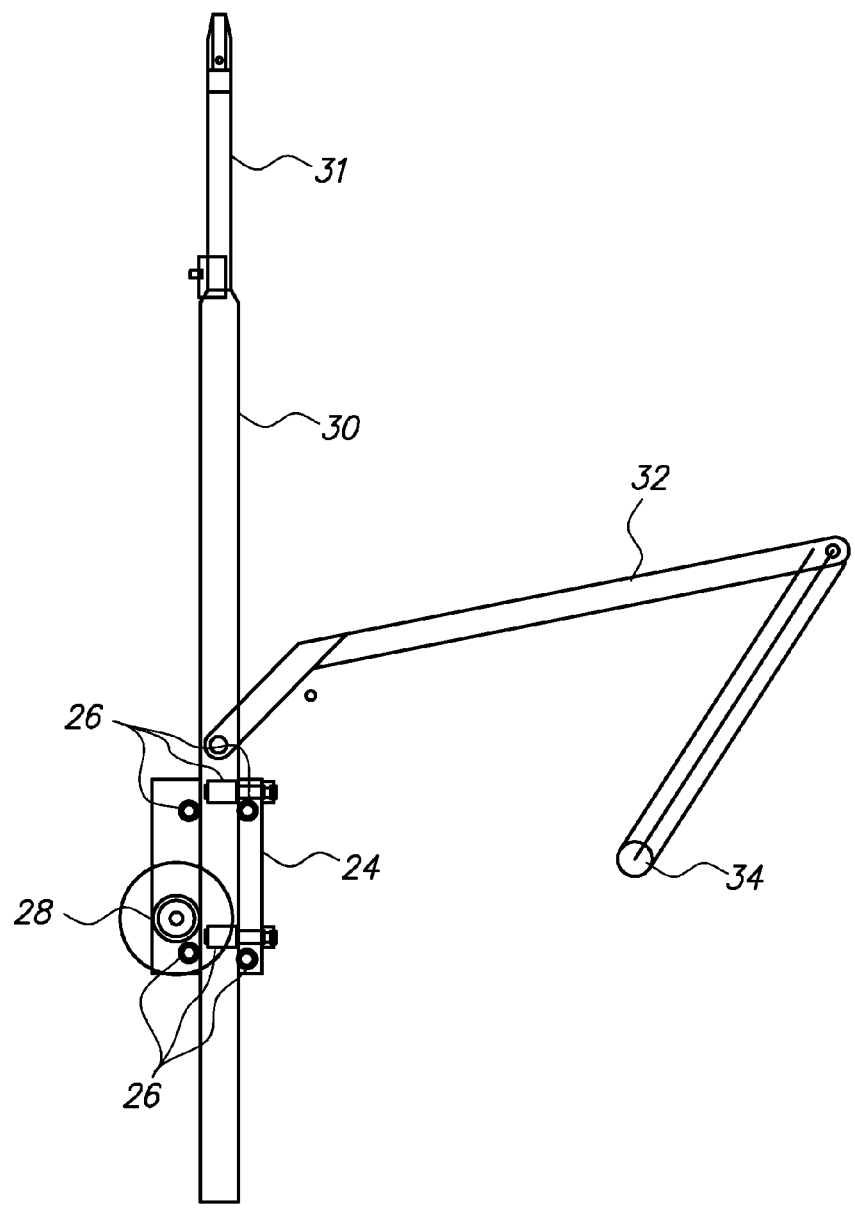
FIG. 3A is a side elevational view of a sampler assembly in the drive position according to a preferred embodiment of the present invention.
Figure 3B:
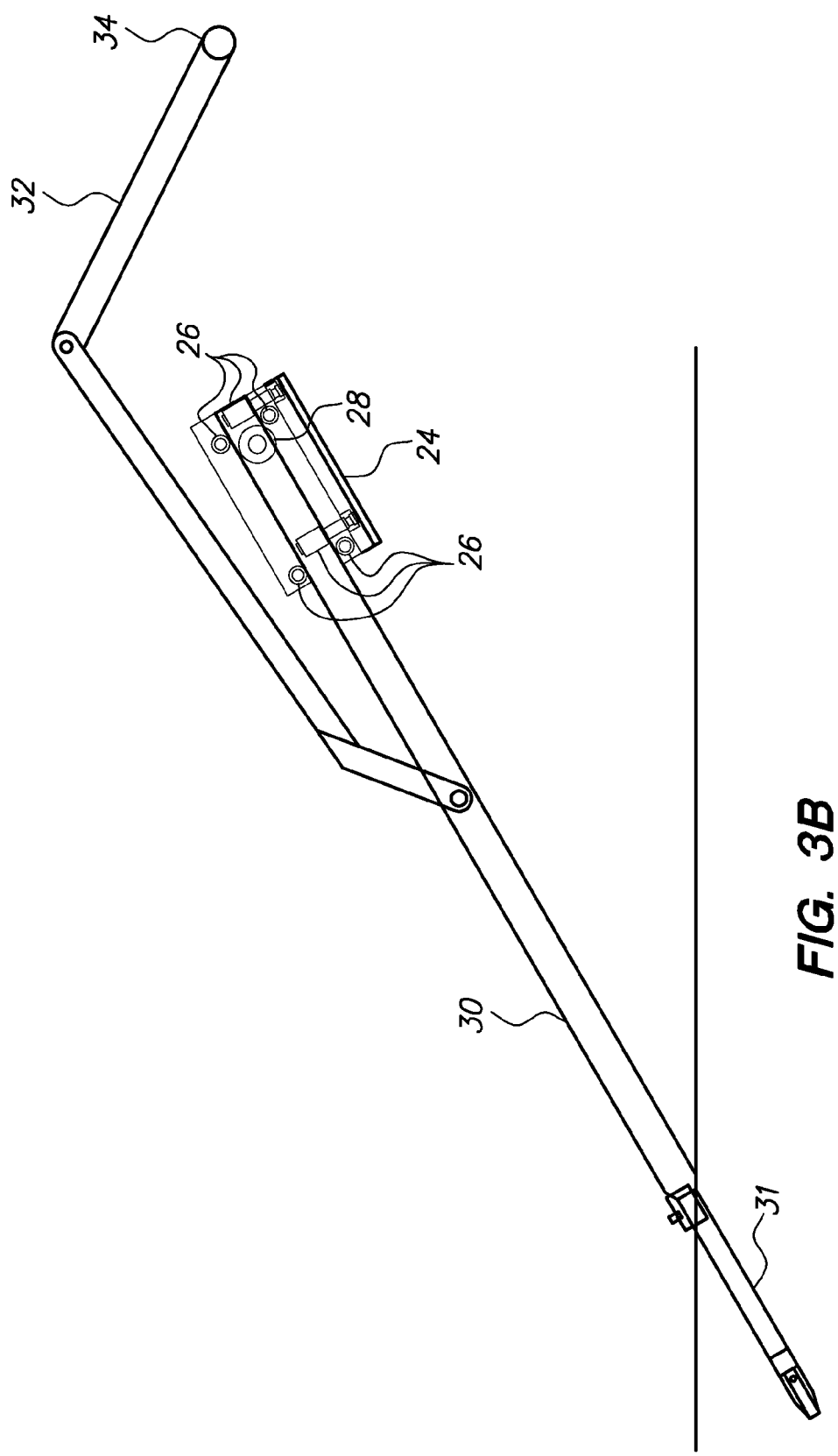
FIG. 3B is a side elevational view of a sampler assembly in the collection position according to a preferred embodiment of the present invention.

Turning now to FIGS. 3A and 3B, the probe components of sampling assembly 14 may be described in greater detail. It may be noted that the components shown in FIGS. 3A and 3B are repeated on each side of bed 12 of vehicle 10 in the preferred embodiment, although in alternative embodiments only one probe mechanism may be employed. Arm guide plate 24, which preferably is formed in an "L" shape, is mounted to vehicle 12 by means of guide plate axle 28. Guide plate 24 may turn freely about the axis of guide plate axle 28, a roller bearing (not shown) preferably being employed in a known manner to reduce friction. Probe arm 30 is fitted to guide plate 24 and held in place by guide plate rollers 28. Guide plate rollers 28 allow probe shaft 30 to move longitudinally with respect to guide plate 24, the purpose of which will be described below. In the preferred embodiment, there are a total of six guide plate rollers 28 on each guide plate 24, with two of the rollers being forward of probe shaft 30, two being rearward of probe arm 30, and two being to the outside of probe shaft 30. Since guide plate 24 itself fits against probe arm 30 on its fourth side, it may be seen that probe shaft 30 is effectively "trapped" against guide plate 24 in this manner. Probe shaft 30 may thus move longitudinally with respect to guide plate 24, with the various guide plate rollers 28 turning as it does so, but may not move laterally with respect to guide plate 24. Probe 31 is attached at the distal end of probe shaft 30, its design being described in more detail below Probe arm 32 is rotatably connected to probe shaft 30 at a point between the connection of probe shaft 30 and guide plate axle 28 and the connection of probe shaft 30 with probe 31. Probe arm 32 is preferably formed in hinged sections, with probe arm 32 being formed in three sections, two being hinged together, in the preferred embodiment. Probe arm 32 is connected at probe arm axle 34 in a rotatable manner, and linked to hydraulic cylinder 22. It may be seen that in this manner, the extension of hydraulic cylinder 22 causes an extension of probe arm 32 forwardly, which in turn causes probe arm 32 to rotate counterclockwise about guide plate axle 28. Simultaneously, probe arm 32 extends outwardly, causing an extension of probe arm 32 into the soil. As a result, probe 31 is turned to point downwardly into the soil in order to collect a soil sample, as shown in FIG. 3B. Retraction of hydraulic cylinder 22 results in a reversal of this operation, such that probe 31 returns to the rest position, pointed upwardly, as shown in FIG. 3A.

Figure 7:
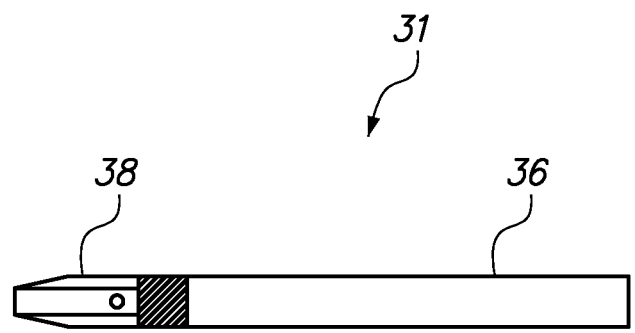
FIG. 7 is a side elevational view, in partial cut-away, of the probe according to a preferred embodiment of the present invention.

Turning now to FIG. 7, the structure of probe 31 may be described in more detail. Probe 31 comprises a hollow tube 36 designed to receive soil upon its insertion into the ground during sampling operation. Probe 31 may be constructed of any sufficiently rigid and durable material, such as steel. Probe tip 38 is attached at the distal end of probe 31. In alternative embodiments, probe tube 36 and probe tip 38 may be constructed as a single part, although it is preferred that they are separate so that probe tip 38 may be easily replaced as it wears or is damaged during sampling operations. It will be noted that the interior of probe tip 38 in the preferred embodiment is sloped such that the inner diameter increases as soil pushes into tip 38. Because soil is dumped from the proximal end of tube 36 during the collection process as described below, it will be seen that this design serves to prevent soil compaction as the soil is being moved from an area of more restricted diameter to an area of greater diameter during removal.

Figure 4:
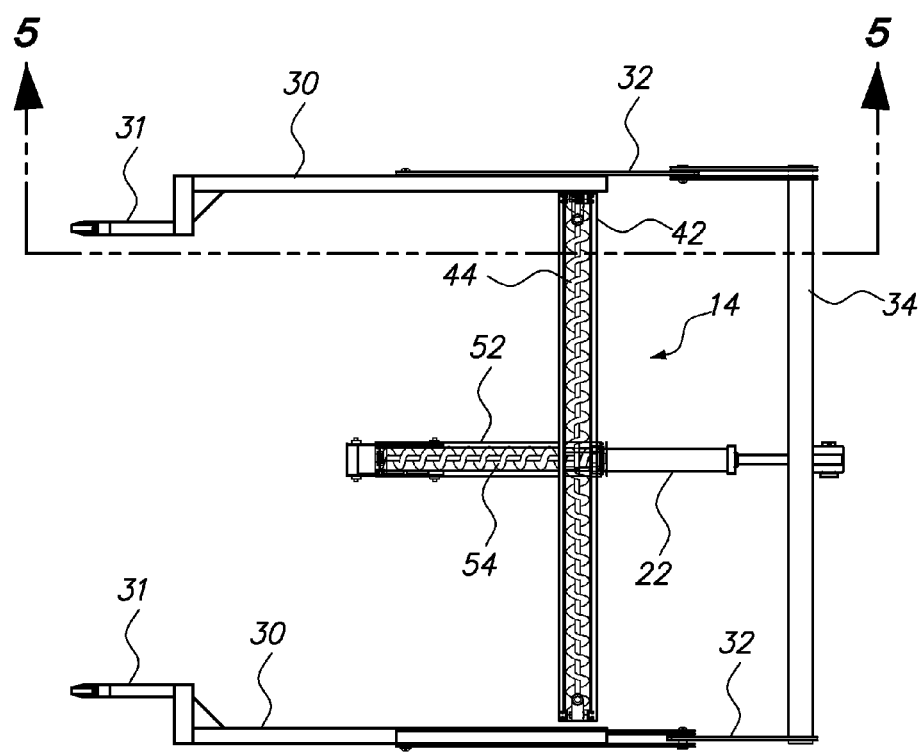
FIG. 4 is a top plan view of the sampling and collection assemblies according to a preferred embodiment of the present invention.
Figure 5:
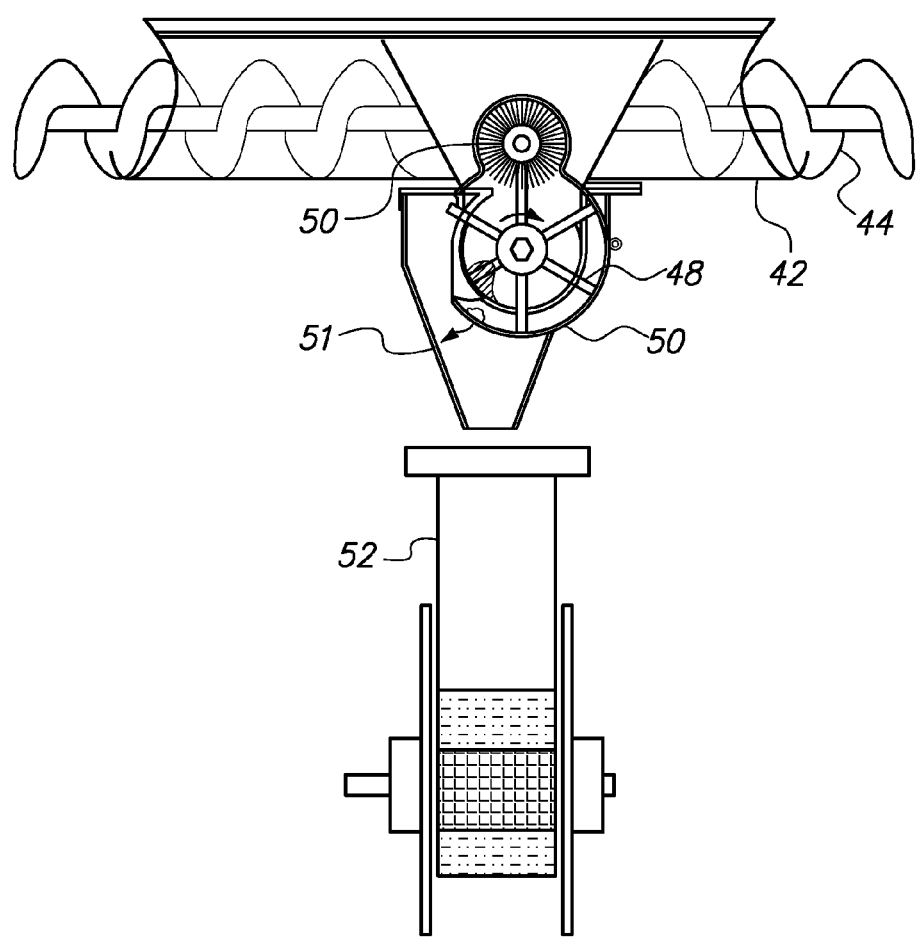
FIG. 5 is a detail, side elevational view, in partial cut-away, of the collection assembly according to a preferred embodiment of the present invention.

Turning now to FIGS. 4 and 5, the process of collecting soil from probe 31 into sampling assembly 14 may be described. It may be seen that the longitudinal axis of probe 31 is set towards the centerline of the apparatus relative to the centerline of probe shaft 30. As a result, there is no impediment to soil that is collected in tube 36 of probe 31 to simply fall from probe 31 as probe 31 is returned to the position shown in FIG. 3A due simply to gravity. In the preferred embodiment, a stop 40 (shown in FIG. 2) may be employed to halt the clockwise rotation of probe shaft 30 as it returns to the position shown in FIG. 3A, and to provide a "bump" that helps to dislodge soil from tube 36 of probe 31. It may be seen in FIG. 4 that when probe 31 reaches the position shown in FIG. 3A, soil falling from probe 31 will drop into transverse auger tray 42. The rotation of transverse auger 44 within transverse auger tray 42 will cause the soil to be drawn towards the centerline of the apparatus, where it will drop down through an opening in the center of transverse auger tray 42.

As shown in FIG. 5, soil passing through such opening will enter rotor housing 46, wherein rotor 48 is located. The purpose of rotor 48 is to regulate the flow of soil into bagging assembly 20. Rotor 48 is preferably powered by a hydraulic motor (not shown), as are well known in the prior art. In the preferred embodiment, the upper sidewalls of rotor housing 46 are carved out to match a hole in the bottom of transverse auger tray 42. The blades of rotor 48 extend far enough that they pass into the carved out portion of rotor housing 46, and thus extend into the interior of transverse auger tray 42. As a result, soil that passes through transverse auger tray 42 into rotor housing 46 does not simply fall into rotor housing 46 from above, but instead is fed directly into the blades of rotor 48 due to the action of transverse auger 44. It is believed that this design provides a more reliable, positive feed of soil samples from transverse auger tray 42 through rotor housing 46. Soil that reaches rotor housing 46 is forced from the top section of rotor housing 46 to the bottom section of rotor housing 46 as a result of the rotation of the blades of rotor 48. In the preferred embodiment, cleaning brush wheel 50 may be mounted adjacent to rotor 48 such that the rotation of rotor 48 causes the blades of rotor 48 to push against rotor brush wheel 50. The purpose of rotor brush wheel 50 is to keep the blades of rotor 48 clean of moist soil that might otherwise cling to the blades of rotor 48 and thereby degrade the operation of the apparatus.

Figure 6:
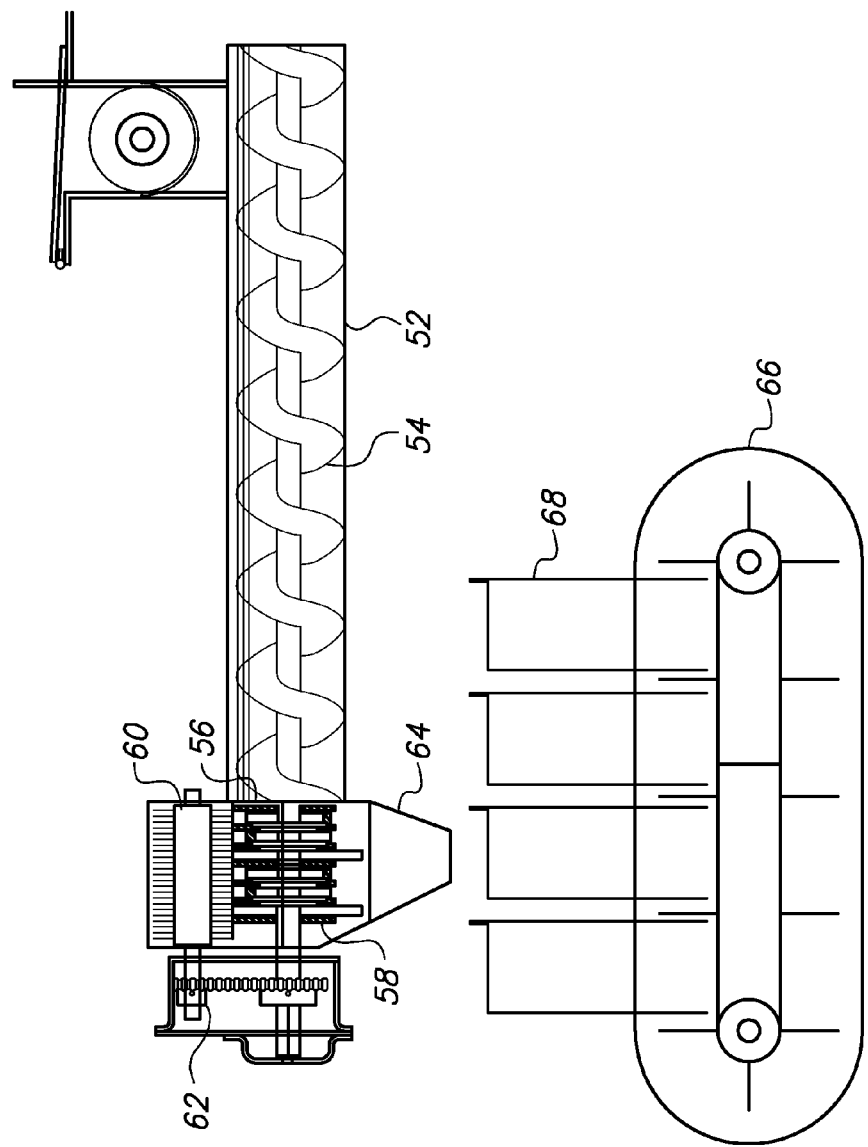
FIG. 6 is a side elevational view, in partial cut-away, of the bagging assembly according to a preferred embodiment of the present invention.

Soil drawn into rotor housing 46 by rotor 48 is pushed by rotor 48 down through transverse auger tray funnel 51 and into longitudinal auger tray 52. The soil is then delivered by longitudinal auger 54 towards bagging assembly 20 positioned in cab 18, as shown in FIG. 6. The soil is delivered by longitudinal auger 54 to chopping blade housing 56. Chopping blades 58 rotate without chopping blade 56. In the preferred embodiment, chopping blades 58 comprise a series of blades of different lengths for the purpose of cutting any sticks or other organic material that may have been collected with the soil sample and delivered to chopping blade housing 56. The result of passing the soil through chopping blades 58 will be the reduction of such material to small particles that will not interfere with the analysis of the resulting soil samples. Chopping blade brush wheel 60, driven by gear mechanism 62 from the rotation of longitudinal auger 54, serves to keep chopping blades 56 clean in a manner similar to that of rotor 48 as described above. Soil passing through chopping blade housing 56 falls through longitudinal auger funnel 64 and into one of the bags 68 on bagging tray 66. Preferably, bagging tray 66 rotates to present another bag for collection as soon as the previous bag is filled. The operator or operators may then place empty bags in place of each filled bag during a continuous sampling operation.

As used herein, "comprising" is synonymous with "including," "containing," or "characterized by," and is inclusive or open-ended and does not exclude additional, unrecited elements or method steps. As used herein, "consisting of" excludes any element, step, or ingredients not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

When a Markush group or other grouping is used herein, all individual members of the group and all combinations and subcombinations possible of the group are intended to be individually included in the disclosure.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Thus, additional embodiments are within the scope of the invention and within the following claims.

In general the terms and phrases used herein have their art-recognized meaning, which can be found by reference to standard texts, journal references and contexts known to those skilled in the art. The preceding definitions are provided to clarify their specific use in the context of the invention.

All patents and publications mentioned in the specification are indicative of the levels of skill of those skilled in the art to which the invention pertains. All references cited herein are hereby incorporated by reference to the extent that there is no inconsistency with the disclosure of this specification.

The present invention has been described with reference to certain preferred and alternative embodiments that are intended to be exemplary only and not limiting to the full scope of the present invention as set forth in the appended claims.

What is claimed is:

1. A soil sampling apparatus, comprising:
   (a) a motorized vehicle, wherein said motorized vehicle comprises a bed and a cab;
   (b) a probe assembly mounted to said bed of said vehicle, wherein said probe assembly comprises a soil sample probe, and wherein said probe assembly is rotatable and extendible to move from a first upright, retracted position to a second downwardly pointed, extended position whereby said probe is extended into the soil;
   (c) a collection assembly mounted to said bed of said vehicle, wherein a portion of said collection assembly extends into said cab of said vehicle, and whereby soil deposited in said probe assembly may be collected; and
   (d) a bagging assembly mounted to said cab of said vehicle, whereby soil deposited from said collection assembly may be bagged for later analysis.

2. The soil sampling apparatus of claim 1, wherein said probe assembly comprises a probe shaft pivotally connected to said motorized vehicle.

3. The soil sampling apparatus of claim 2, further comprising a guide plate rotatably connecting said probe shaft and said vehicle, wherein said probe shaft may extend and retract with respect to said guide plate.

4. The soil sampling apparatus of claim 3, further comprising at least one roller attached to said guide plate and in contact with said probe shaft.

5. The soil sampling apparatus of claim 2, further comprising a probe arm connected to said probe shaft and to said vehicle.

6. The soil sampling apparatus of claim 5, wherein said probe arm is hingeably articulated.

7. The soil sampling apparatus of claim 6, further comprising a hydraulic cylinder in communication with said probe arm.

8. The soil sampling apparatus of claim 1, wherein said probe comprises a probe tip comprising a distal end and a hollow interior having a diameter that is greater at a point further from said distal end of said tip than appoint closer to said distal end of said tip.

9. The soil sampling apparatus of claim 8, wherein said probe further comprises a hollow tube attached to said probe tip, and wherein said probe tip is removably attached to said hollow tube.

10. The soil sampling apparatus of claim 1, further comprising a plurality of probe assemblies.

11. The soil sampling apparatus of claim 1, wherein said collection assembly comprises a transverse auger tray positioned beneath said probe when said probe is in said first position.

12. The soil sampling apparatus of claim 11, wherein said collection assembly further comprises an auger positioned within said transverse auger tray.

13. The soil sampling apparatus of claim 12, wherein said collection assembly further comprises a rotor within a rotor housing, said rotor positioned beneath and extending partially into said transverse auger tray such that said transverse auger is operable to deliver soil to said rotor.

14. The soil sampling apparatus of claim 13, wherein said collection assembly further comprises a rotor brush in contact with said rotor and operable to clean said rotor.

15. The soil sampling apparatus of claim 13, wherein said collection assembly further comprises a longitudinal auger tray beneath said rotor housing.

16. The soil sampling apparatus of claim 15, wherein said collection assembly further comprises a longitudinal auger with said longitudinal auger tray.

17. The soil sampling apparatus of claim 16, further comprising at least one chopping blade with a chopping blade housing, said chopping blade positioned at an end of said longitudinal auger tray such that said longitudinal auger is operable to deliver soil to said chopping blade.

18. The soil sampling apparatus of claim 17, further comprising a chopping blade brush in contact with said chopping blade and operable to clean said chopping blade.

19. The soil sampling apparatus of claim 17, wherein said bagging assembly further comprises a rotatable bag tray positioned beneath said chopping blade housing to receive soil from said chopping blade assembly.

20. The soil sampling apparatus of claim 19, further comprising a plurality of bags positioned on said bag tray.

* * * * *